United States Patent
Weinberg et al.

(10) Patent No.: US 12,290,467 B2
(45) Date of Patent: May 6, 2025

(54) DRAINABLE OSTOMY POUCH INCLUDING CLOSURE MEMBERS AND METHOD OF MAKING THE SAME

(71) Applicant: Hollister Incorporated, Libertyville, IL (US)

(72) Inventors: Robert J. Weinberg, Lake Villa, IL (US); Timothy A. Friske, Antioch, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 629 days.

(21) Appl. No.: 17/438,978

(22) PCT Filed: Apr. 15, 2020

(86) PCT No.: PCT/US2020/028217
§ 371 (c)(1),
(2) Date: Sep. 14, 2021

(87) PCT Pub. No.: WO2020/226861
PCT Pub. Date: Nov. 12, 2020

(65) Prior Publication Data
US 2022/0142808 A1    May 12, 2022

Related U.S. Application Data

(60) Provisional application No. 62/842,721, filed on May 3, 2019.

(51) Int. Cl.
*A61F 5/44*    (2006.01)
*A61F 5/445*    (2006.01)

(52) U.S. Cl.
CPC ............ *A61F 5/4407* (2013.01); *A61F 5/445* (2013.01)

(58) Field of Classification Search
CPC ...... A61F 5/4407; A61F 5/445; A61F 5/4405; A61F 5/442; B65B 69/0008;
(Continued)

(56) References Cited

U.S. PATENT DOCUMENTS

| | | | |
|---|---|---|---|
| 2,281,027 A * | 4/1942 | Dennison | .................. E04C 2/26 156/308.2 |
| 3,523,534 A | 8/1970 | Nolan | |

(Continued)

FOREIGN PATENT DOCUMENTS

| | | |
|---|---|---|
| WO | 03086250 A1 | 10/2003 |
| WO | 2018136793 A1 | 7/2018 |

OTHER PUBLICATIONS

International Preliminary Report on Patentability issued by International Bureau of WIPO in connection with PCT/US2020/028217 on Nov. 2, 2021.

(Continued)

*Primary Examiner* — Catharine L Anderson
*Assistant Examiner* — Quynh Dao Le
(74) *Attorney, Agent, or Firm* — Klintworth & Rozenblat IP LLP

(57) ABSTRACT

A method of making drainable ostomy pouch outlet includes the steps of attaching a single-piece closure device on a downwardly extending outlet portion of the pouch and trimming side peripheries of the single-piece closure device to provide at least two separate closure members. The single-piece closure device may include at least one transversely-extending cut-line and/or at least one cut-out portions, which may be arranged to form at least two separate closure members on the outlet portion after the step of trimming.

10 Claims, 4 Drawing Sheets

(58) Field of Classification Search
CPC .......... B65B 69/0016; Y10T 156/1084; Y10T 156/1089; Y10T 24/15; Y10T 156/00; Y10T 156/1052; Y10T 156/108; Y10T 156/1043; Y10T 156/1062; Y10T 156/1064; Y10T 156/1066; Y10T 156/12; Y10T 156/1317; B65D 33/1658; B65D 33/1625; B65D 33/246
USPC ........ 604/332, 334, 335; 156/159, 250, 257, 156/258
See application file for complete search history.

(56) References Cited

U.S. PATENT DOCUMENTS

| | | | |
|---|---|---|---|
| 4,411,659 A | 10/1983 | Jense | |
| 6,419,664 B1* | 7/2002 | von Bulow | A61F 5/4407 604/327 |
| 7,879,015 B2 | 2/2011 | Villefrance et al. | |
| 8,672,907 B2 | 3/2014 | Friske et al. | |
| 8,920,590 B1* | 12/2014 | Cummings | B32B 37/1292 156/267 |
| 9,011,395 B2 | 4/2015 | Friske et al. | |
| 2002/0088080 A1* | 7/2002 | Fenton | A61F 5/445 604/338 |
| 2004/0216830 A1* | 11/2004 | Van Eperen | B29C 66/83411 156/251 |
| 2006/0196787 A1* | 9/2006 | Lewis | B65D 33/1658 206/232 |
| 2008/0114319 A1* | 5/2008 | Burns | A61F 13/15739 604/385.01 |
| 2013/0253456 A1 | 9/2013 | Friske | |
| 2016/0135983 A1* | 5/2016 | Murray | A61F 5/4407 604/335 |
| 2017/0209297 A1* | 7/2017 | Lysgaard | A61F 5/4404 |
| 2018/0333290 A1* | 11/2018 | Jones | A61F 5/441 |

OTHER PUBLICATIONS

International Search Report issued by ISA/EPO in connection with PCT/US2020/028217 on Jun. 22, 2020.

Written Opinion issued by ISA/EPO in connection with PCT/US2020/028217 on Jun. 22, 2020.

* cited by examiner

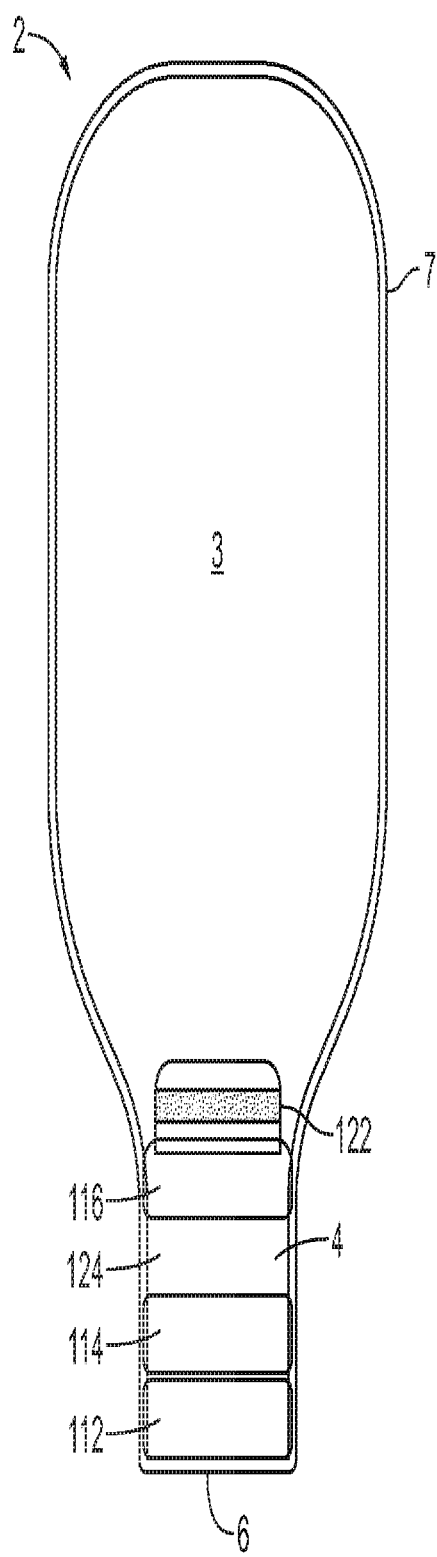
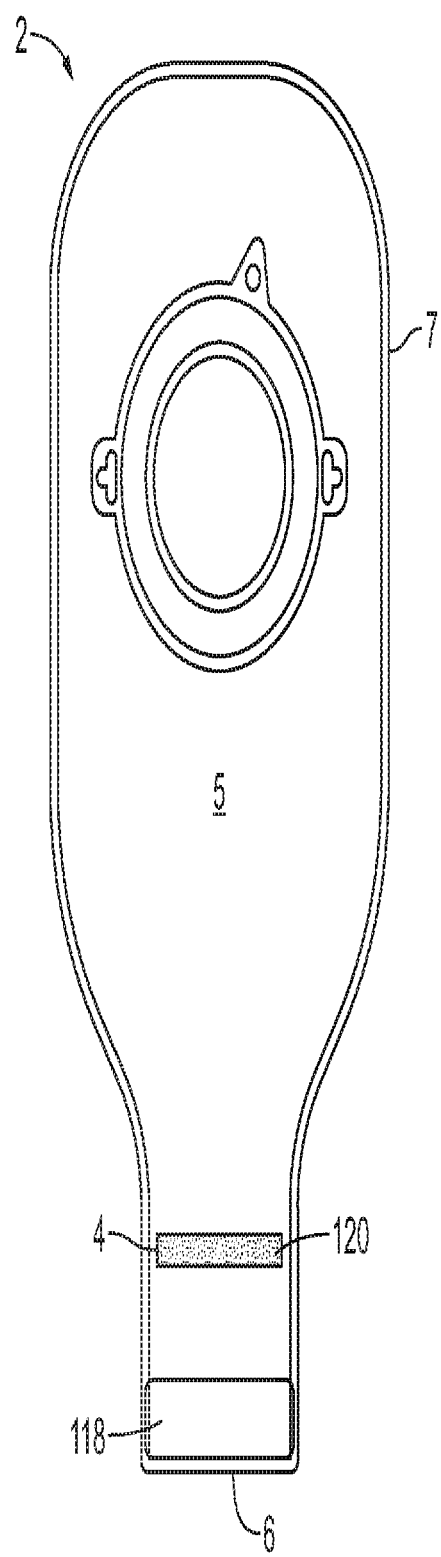
FIG. 3
(Prior Art)
FIG. 4
(Prior Art)

DRAINABLE OSTOMY POUCH INCLUDING CLOSURE MEMBERS AND METHOD OF MAKING THE SAME

This is a National Stage Application of International Patent Application No. PCT/US2020/028217, filed Apr. 15, 2020, which claims the benefit of and priority to U.S. Provisional Application No. 62/842,721, filed May 3, 2019, the entireties of which are incorporated fully herein by reference.

BACKGROUND

The present disclosure generally relates to ostomy appliances, and more particularly to drainable ostomy pouches having closure systems.

Ostomy pouches for collecting body waste are used by patients who have had surgery such as a colostomy, ileostomy, or urostomy. Ostomy pouches typically include flat, opposing side walls secured together along their edges to define a collection cavity. One of the side walls is provided with an opening to receive a stoma, and means to secure the pouch to the user, such as an adhesive barrier, so that body waste discharged through the stoma is received within the cavity.

The ostomy pouch may be a closed-end pouch for a single use, in which case the entire pouch is discarded after it has been substantially filled with stomal discharge. Alternatively, the ostomy pouch can be a drainable pouch with a discharge opening at its lower end, which may be closed during collection of body waste material but may be opened for draining body waste material from the pouch after a period of use. Such drainable pouches are disclosed, for example, in Nolan, U.S. Pat. No. 3,523,534, and Jensen et al., U.S. Pat. No. 4,411,659, which are incorporated herein in their entirety by reference.

The discharge opening of drainable pouches is typically defined at the end of a narrowed outlet portion, which is provided with closure means for maintaining the discharge opening in a sealed condition until waste material is to be drained from the pouch. The closure means may take the form of a clamp, as in the aforementioned Nolan patent, or a device such as conventional wire ties or wraps for securing the outlet portion in an upwardly-rolled condition.

For quality of life of the users, drainable pouches should be easy to drain without risking soiling of clothes or the surroundings. They also should be easy to close securely after being drained and amenable to being cleaned after drainage and before closing again, such that the risk of unpleasant odor is substantially reduced. Most importantly, the closure means should provide a secure seal when closed to minimize the risk of leakage.

Many different solutions concerning the closing, cleaning and drainage operations have been proposed and implemented. For example, Villefrance et al., U.S. Pat. No. 7,879,015, Friske et al., U.S. Pat. No. 8,672,907, and Friske et al. U.S. Pat. No. 9,011,395, which are commonly assigned with the present application and incorporated herein in their entirety by reference, disclose drainable pouches having integral closure systems. In drainable pouches including more than one closure members, such as those disclosed in Friske et al. U.S. Pat. No. 9,011,395, the closure members typically need to be attached to a pouch outlet within relatively tight tolerances for a liquid-tight seal of the outlet in a folded-up, closed position. For example, the closure members may be arranged with a gap therebetween, which may need to be controlled within a relatively tight tolerance. Manufacturing of such drainable pouches may involve relatively complex assembly process steps for placement and attachment of the closure members within the required tolerances.

The present disclosure provides an improved method of making drainable pouches including multiple closure members and drainable pouch formed using such a method.

BRIEF SUMMARY

In one aspect, a method of making a drainable ostomy pouch is provided. The method may include the step of providing a drainable pouch including a bodyside wall, a distal wall, and a downwardly extending outlet portion, the step of providing a single-piece closure device configured to form at least two closure members, the step of attaching the single-piece closure device on the downwardly extending outlet portion, and the step of trimming peripheries of the single-piece closure device to form at least two separate closure members. In the step of providing the drainable pouch, the bodyside wall and the distal wall may be joined along peripheral edges to define a cavity therebetween for collecting stomal discharge, and the downwardly extending outlet portion may terminate in a discharge opening for draining stomal discharge contents collected in the cavity. The at least two separate closure members may be configured to facilitate folding up of the outlet portion and providing a liquid tight seal in a closed position.

In an embodiment, the single-piece closure device may include at least one transversely-extending cut-line and at least one uncut portion arranged at a peripheral end of the transversely-extending cut-line. For example, the single-piece closure device may include one transversely-extending cut-line and two uncut portions. The transversely-extending cut-line may be arranged to divide the single-piece closure device into first and second portions, wherein each of the uncut portions may be arranged at each peripheral end of the transversely-extending cut-line to hold the first and second portions together.

In some embodiments, the single-piece closure device may also include at least one fold-line configured to facilitate opening of the discharge opening. The at least one fold-line may extend from an upper periphery of the single-piece closure device to a lower periphery of the single-piece closure device, wherein the closure members may be configured to bend along the at least one fold-line when pressure is applied along the peripheral edges of the outlet portion to open the discharge opening. In an embodiment, the at least one fold-line may include four slanted fold-lines, wherein the slanted fold-lines may be configured and arranged such that a distance between the slanted fold-lines proximate the lower periphery is smaller than that of proximate the upper periphery. The slanted fold-lines may be configured to bend outwardly when pressure is applied along the peripheral edges of the outlet portion to open the discharge opening.

In another embodiment, the single-piece closure device may include at least one cut-out portion configured and arranged to form at least two closure members with at least one gap therebetween. For example, the single-piece closure member may include two cut-out portions and an uncut portion arrange at each peripheral end of each of the cut-out portions. Such a single-piece closure member may be configured to provide three separate closure members with a gap between the adjacent closure members.

In an embodiment, the single-piece closure device may be provided having a width greater than a width of the downwardly extending outlet portion. In such an embodiment, the step of trimming side peripheries of the single-piece closure device may include cutting off side peripheral portions of the single-piece closure device including at least one uncut portion, such that each of the at least two separate closure members formed after the step of trimming has a width less than or equal to the width of the downwardly extending outlet portion.

The step of attaching the single-piece closure device may be performed before pouch films are die cut to a drainable pouch shape. In such an embodiment, the step of trimming side peripheries of the single-piece closure device and die cutting of the drainable pouch shape may be performed together in a single die-cutting step.

Alternatively, the step of attaching the single-piece closure device may be performed after pouch films are die cut to a drainable pouch shape. In such an embodiment, the step of trimming side peripheries of the single-piece closure device may involve cutting the side peripheries of the single-piece closure device to match side peripheries of the downwardly extending outlet portion.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein:

FIG. 3 is a distal side view of a prior art drainable ostomy pouch including closure members and fastener strips;

FIG. 4 is a body side view of the prior art drainable ostomy pouch of FIG. 3;

DETAILED DESCRIPTION

Figure 1:
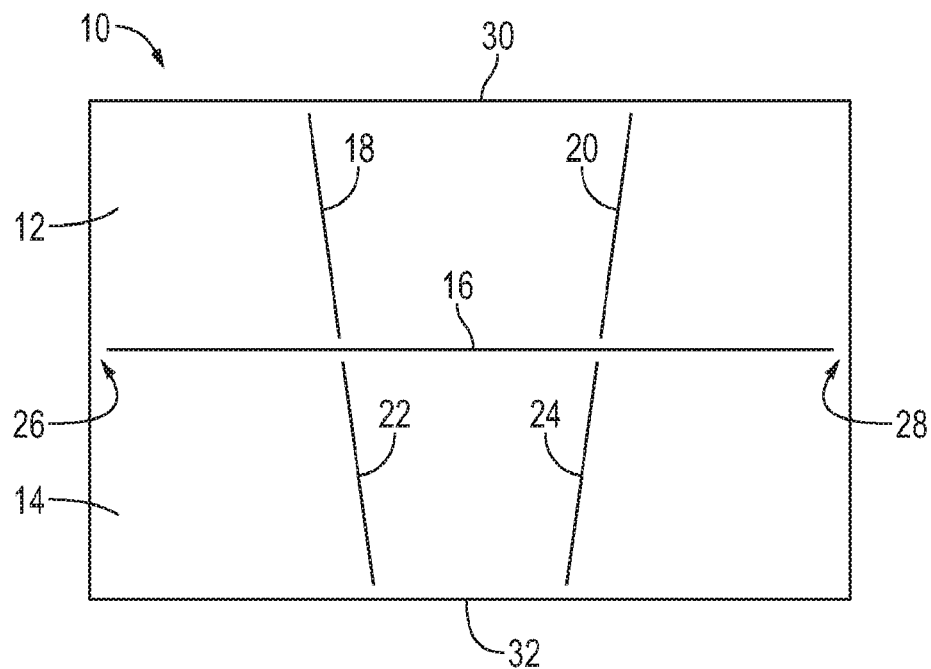
FIG. 1 is a schematic illustration of a single-piece closure device for a drainable ostomy pouch according to an embodiment.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated. The words "a" or "an" are to be taken to include both the singular and the plural. Conversely, any reference to plural items shall, where appropriate, include the singular.

Referring now to the figures, FIG. 1 shows a single-piece closure device 10 for a drainable pouch according to an embodiment. The closure device 10 may be configured to form at least two separate closure members 12, 14 when attached to a drainable pouch outlet portion 4 (FIG. 2) according to various embodiments of a method of making a drainable pouch described in the present disclosure. The closure device 10 may be formed as a single-piece device including at least one transversely-extending cut line 16. The at least one transversely-extending cut-line 16 may be defined by at least one through-cut cutting through the thickness of the closure device 10. At least one uncut portion 26, 28 may be arranged at a peripheral end of each of the at least one transversely-extending cut-line to hold the closure device 10 in a single-piece configuration.

In the embodiment of FIG. 1, the closure device 10 may include one transversely-extending cut-line 16 dividing the closure device 10 into first and second portions configured to form first and second closure members 12, 14. In this embodiment, a first uncut portion 26 may be arranged at one peripheral end of the transversely-extending cut-line 16, and a second uncut portion 28 may be arranged at the other end of the transversely-extending cut-line 16. The first and second uncut portions may be configured and arranged to hold the first and second portions together to maintain the closure device 10 in a single-piece configuration. In other embodiments, the closure device 10 may include two or more transversely-extending cut-lines configured and arranged to form three or more closure members.

The closure device 10 may also include a plurality of fold-lines 18, 20, 22, 24, which may be configured to facilitate opening of the pouch outlet 4. In an embodiment, each of the fold-lines 18, 20, 22, 24 may be provided as slanted lines or sloped lines, which may be arranged and aligned to facilitated opening of the pouch outlet 4. In the embodiment of FIG. 1, the closure member 10 includes four fold-lines 18, 20, 22, 24, wherein the fold-lines 18, 22 are aligned to form a first larger slanted fold-line and the fold-lines 20, 24 are aligned to form a second larger slanted fold-line, wherein a distance between the fold-lines 22, 24 proximate a lower periphery 32 of the closure device 10 is smaller than a distance between the fold-lines 18, 20 proximate an upper periphery 32 of the closure device 10. The fold-lines 18, 20, 22, 24 may be arranged and configured to bend outwardly when pressure is applied along the peripheral edges of the pouch outlet 4. The fold-lines 18, 20, 22, 24 may be defined by creases or cuts in the closure device 10.

The closure device 10 may be formed from a suitable thin material, such as thin single or multilayer polymeric materials having a thickness of about 2 mil to about 40 mil, preferably about 15 mil to about 25 mil, and more preferably about 20 mil. For example, the single-piece closure member 22 may be formed from a multilayer polymeric material.

Figure 2:
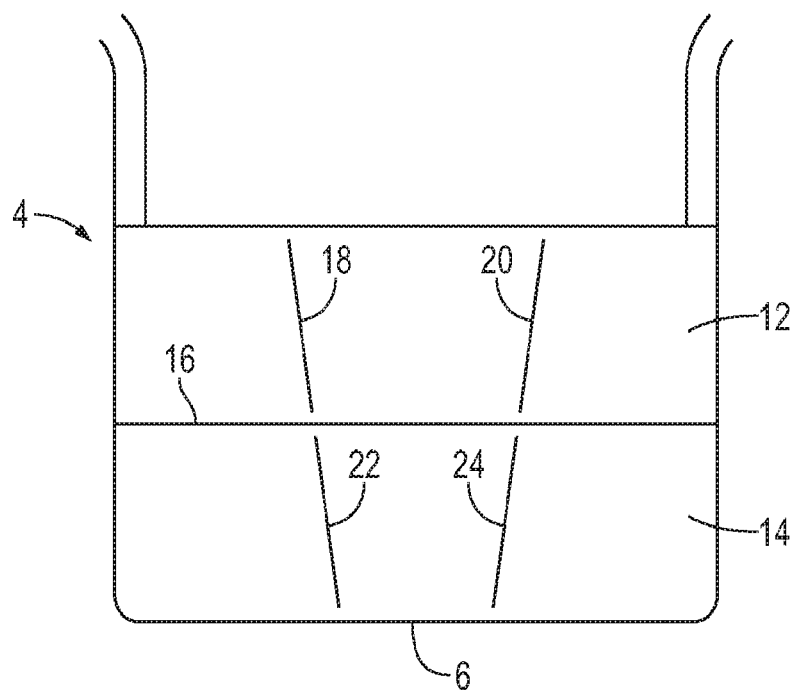
FIG. 2 is a schematic illustration of a drainable pouch outlet including closure members formed from the single-piece closure device of FIG. 1 using a method of making a drainable ostomy pouch according to an embodiment.
Figure 5:
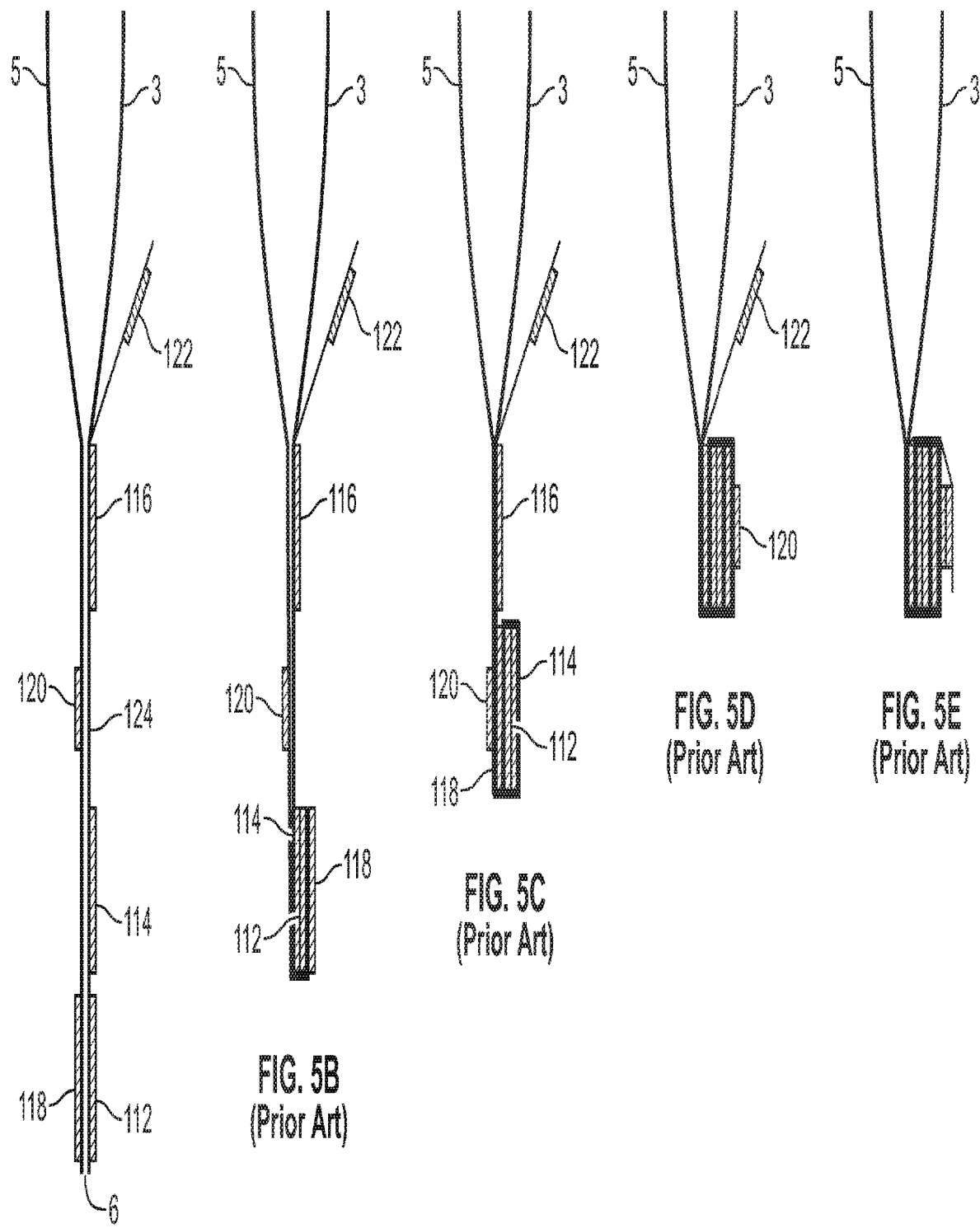
FIGS. 5A-5E are schematic cross-sectional views of the prior art drainable ostomy pouch of FIG. 3 illustrating an outlet portion being folded up for closure.

In a method of making a drainable pouch according to an embodiment, the closure device 10 having a width greater than a width of a pouch outlet portion 4 may be provided. The closure device 10 may be attached to the pouch outlet portion 4, and side peripheries of the closure device 10 including the uncut portions 26, 28 may be trimmed off to provide the two separate closure members 12, 14 on the pouch outlet 4 as shown in FIG. 2.

The closure device 10 may be attached to a pouch film prior to the pouch film being die cut to a pouch shape. In such an embodiment, the side trimming of the closure member 10 and die cutting of the pouch film may be performed in a single die-cutting step. Alternatively, the closure device 10 may be attached to a pouch outlet portion 4 after the pouch film has been die-cut into the pouch shape. In such an embodiment, the side trimming of the closure member 10 may be performed separately from the die-cutting step of the pouch film. The closure device 10 may be attached to the pouch film using a known method, such as via an adhesive, heat sealing, ultrasonic welding, laser welding, etc. The method of making a drainable pouch according to various embodiments of the present disclosure may simplify the manufacturing process and improve quality of the drainable pouch by reducing or eliminating the need for separate placement and attachment of the closure members.

FIGS. 3 and 4 show a prior art ostomy drainable pouch 2. The drainable pouch 2 includes a distal wall 3 and a bodyside wall 5, which are joined along their peripheral edges 7 to define a cavity therebetween for collecting stomal discharge. The drainable pouch 2 includes a downwardly extending outlet 4 terminating in a discharge opening 6. The discharge opening 6 is closed during use by folding the outlet 4 upwardly and securing, it in the upwardly folded position. The walls 3, 5 may be formed of a suitable flexible sheet material, such as a polymeric film, which may be a monolayer or multilayer film.

The drainable pouch 2 includes multiple closure members 112, 114, 116, 118 along outer surfaces of the outlet 4. Each of the closure members 112, 114, 116, 118 is transversely-extending and generally rectangular in its shape. The drainable pouch 2 also includes fastener strips 120, 122. First, second, and third closure members 112, 114, 116 are arranged on a distal surface of the outlet 4, while fourth closure member 118 is arranged on a body-side surface of the outlet 4. The first and second closure members 112, 114 are arranged adjacent and parallel to each other. The third closure 116 is arranged parallel to the second closure member 114 with a gap 124 therebetween.

The closure members 112, 114, 116, 118 are arranged, such that when the outlet 4 is folded up and secured with the fastener strips 120, 122 as shown in FIGS. 5A-5E, the outlet 4 is closed liquid tight. To provide a liquid tight seal, the closure members 112, 114, 116, 118 may need to be arranged relatively precisely within relatively small tolerances, e.g. about 0-0.6 mm. For example, the first and second closure members 112, 114 may need to be arranged with a gap therebetween within a tolerance of about 0.04 mm. Further, the gap 124 between the second and third closure members 114, 116 also may need to be controlled within a tolerance of about 0.04 mm. Thus, the manufacturing of the drainable pouch 2 may involve rather complex steps of placing and attaching of the closure members 112, 114, 116, 118 separately on the outlet 4. Further, such process steps may result in defective pouches that do not provide a liquid tight seal at closure due to variations in the placement of the closure members beyond the required tolerance.

Figure 6:
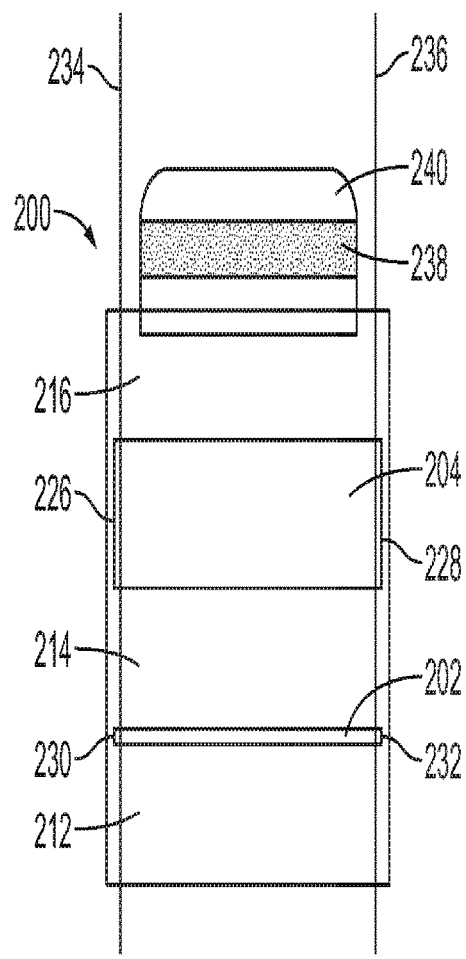
FIG. 6 is a schematic illustration of a single-piece closure device for a drainable ostomy pouch according to another embodiment.

The method of making a drainable pouch using a one-piece closure device according to various embodiments of the present disclosure may reduce or eliminate the process variances due to the separate individual attachment of the closure members and simplify the manufacturing process. FIG. 6 shows a single-piece closure device 200 according to an embodiment. The closure device 200 may be configured to form three separate closure members 212, 214, 216, when a drainable pouch outlet 4 is formed using various embodiments of the method disclosed in the present disclosure.

Figure 7:
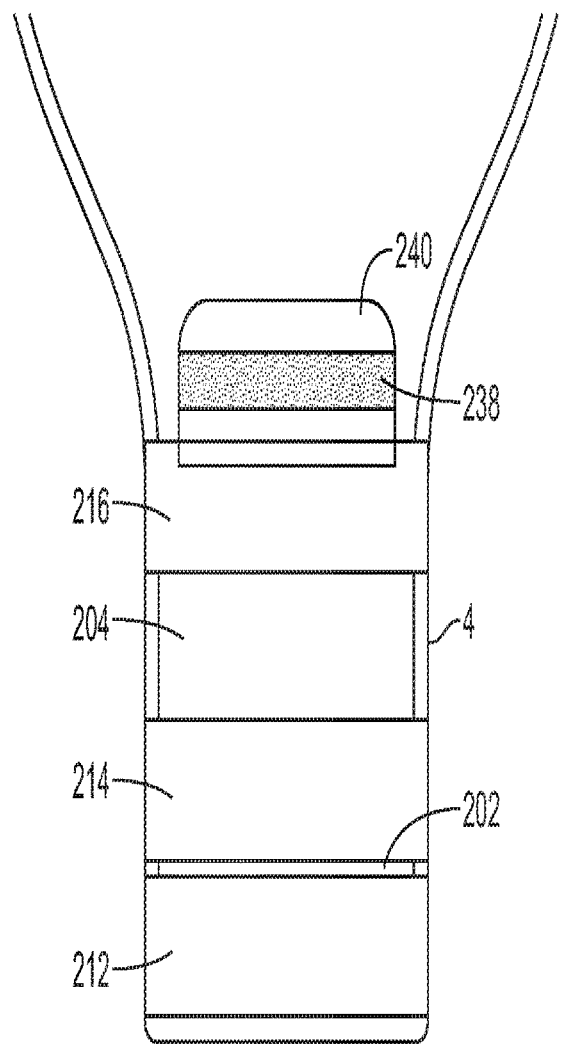
FIG. 7 is a schematic illustration of closure members attached to a drainable pouch outlet formed from the single-piece closure device of FIG. 6.

According to an embodiment, the closure device 200 having a width greater than a width of a pouch outlet portion 4 may be attached to the pouch outlet 4 and side peripheries of the closure device 200 may be trimmed off to provide three separate closure members 212, 214, 216 as shown in FIG. 7. The closure device 200 may be formed as a single-piece device including two cut-out portions 202, 204 configured to define two gaps 202, 204 between closure members 212, 214, 216. The closure device 200 also may comprise uncut portions 226, 228, 230, 232, each of which may be arranged at each peripheral end of the cut-out portions 202, 204 as shown in FIG. 6. The width of the closure device 200 and the width of the uncut portions 226, 228, 230, 232 may be configured such that when the closure device 200 is attached to a pouch outlet portion 4 and trimmed along lines 234, 236, the three separate closure members 212, 214, 216 with the gaps 202, 204 therebetween may be provided on the pouch outlet portion 4. In such an embodiment, the tolerances may be built into the closure device 200, which may be substantially smaller than the variances when attaching the closure members separately as in the prior art drainable pouch of FIG. 3.

In an embodiment, the closure device 200 may further include a fastening strip 238, which may be configured to releasably engage a mating fastening strip (not shown) to secure the outlet portion 4 in a folded-up, closed position, similarly to the prior art drainable pouch of FIGS. 3-5E. In the embodiment of FIG. 6, the fastening strip 238 is provided on a flap 240 and similarly configured to the fastening strip of the prior art drainable pouch of FIG. 3.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A method of making a drainable ostomy pouch comprising the steps of:
   providing a drainable pouch including a bodyside wall, a distal wall, and a downwardly extending outlet portion, wherein the bodyside wall and the distal wall are joined along peripheral edges to define a cavity therebetween for collecting stomal discharge, and the downwardly extending outlet portion terminates in a discharge opening for draining stomal discharge contents collected in the cavity;
   providing a single-piece closure device configured to form at least two closure members;
   attaching the single-piece closure device on the downwardly extending outlet portion; and
   trimming side peripheries of the single-piece closure device to form at least two separate closure members, wherein the side peripheries of the single-piece closure member are trimmed after the single-piece closure device is attached to the downwardly extending outlet portion, wherein the closure members are configured to facilitate folding up of the downwardly extending outlet portion and providing a liquid tight seal in a closed position.

2. The method of claim 1, wherein the single-piece closure device comprises at least one transversely-extending cut-line and at least one uncut portion arranged at a peripheral end of the transversely-extending cut-line.

3. The method of claim 2, wherein the single-piece closure device comprises one transversely-extending cut-line dividing the single-piece closure device into first and second portions and two uncut portions, each of the uncut portions arranged at each peripheral end of the transversely-extending cut-line, wherein the uncut portions configured to hold the first and second portions together.

4. The method of claim 1, wherein the single-piece closure device further comprises at least one fold-line configured to facilitate opening of the discharge opening, wherein the at least one fold-line extends from an upper periphery of the single-piece closure device to a lower periphery of the single-piece closure device, wherein the closure members are configured to bend along the at least one fold-line when pressure is applied along the peripheral edges of the downwardly extending outlet portion to open the discharge opening.

5. The method of claim 4, wherein the at least one fold-line includes four slanted fold-lines, wherein the slanted fold-lines are configured such that a distance between the slanted fold-lines proximate the lower periphery is smaller than that of proximate the upper periphery, wherein the slanted fold-lines are configured to bend outwardly when pressure is applied along the peripheral edges of the outlet portion to open the discharge opening.

6. The method of claim 1, wherein the single-piece closure device includes at least one cut-out portion configured to form at least two closure members with at least one gap therebetween.

7. The method of claim 6, wherein the single-piece closure member includes two cut-out portions and an uncut portion arranged at each peripheral end of each of the cut-out portions, wherein the single-piece closure member is configured to provide three separate closure members with a gap between the adjacent closure members.

8. The method of claim 1, wherein the single-piece closure device has a width greater than a width of the downwardly extending outlet portion, wherein the step of trimming side peripheries of the single-piece closure device includes cutting off side peripheral portions of the single-piece closure device including at least one uncut portion, such that each of the at least two separate closure members formed after the step of trimming has a width less than or equal to the width of the downwardly extending outlet portion.

9. The method of claim 1, wherein the step of attaching the single-piece closure device is performed before pouch films are die cut to a drainable pouch shape, wherein the step of trimming side peripheries of the single-piece closure device and die cutting of the drainable pouch shape is performed together in a single die-cutting step.

10. The method of claim 1, wherein the step of attaching the single-piece closure device is performed after pouch films are die cut to a drainable pouch shape, wherein the step of trimming side peripheries of the single-piece closure device involves cutting the side peripheries of the single-piece closure device to match side peripheries of the downwardly extending outlet portion.

\* \* \* \* \*